(12) United States Patent
Humphreys et al.

(10) Patent No.: US 8,062,865 B2
(45) Date of Patent: Nov. 22, 2011

(54) EXPRESSION CONTROL USING ANTIBODY EXPRESSION OPTIMISATION SEQUENCES

(75) Inventors: David Paul Humphreys, Slough (GB); Mark Ellis, Slough (GB)

(73) Assignee: UCB Pharma S.A., Brussels (BE)

( * ) Notice: Subject to any disclaimer, the term of this patent is extended or adjusted under 35 U.S.C. 154(b) by 192 days.

(21) Appl. No.: 12/089,324

(22) PCT Filed: Sep. 29, 2006

(86) PCT No.: PCT/GB2006/003640
§ 371 (c)(1),
(2), (4) Date: Oct. 3, 2008

(87) PCT Pub. No.: WO2007/039714
PCT Pub. Date: Apr. 12, 2007

(65) Prior Publication Data
US 2009/0239263 A1    Sep. 24, 2009

(30) Foreign Application Priority Data
Oct. 4, 2005 (GB) .................................. 0520169.4

(51) Int. Cl.
*C07H 21/04* (2006.01)
*C12N 1/21* (2006.01)
*C12N 15/63* (2006.01)
*C12P 21/00* (2006.01)

(52) U.S. Cl. ................ 435/69.6; 435/252.33; 435/320.1
(58) Field of Classification Search ................ 435/69.6, 435/252.33, 320.1; 526/25.53
See application file for complete search history.

(56) References Cited

U.S. PATENT DOCUMENTS

| 6,468,738 | B1 | 10/2002 | Kang | |
|---|---|---|---|---|
| 7,419,659 | B2 * | 9/2008 | Popplewell | .................. 424/93.2 |
| 7,452,976 | B2 * | 11/2008 | Popplewell et al. | ....... 530/387.1 |

FOREIGN PATENT DOCUMENTS

| WO | 01/94585 | 12/2001 |
|---|---|---|
| WO | 03/048208 | 6/2003 |

* cited by examiner

*Primary Examiner* — Lynn Bristol
(74) *Attorney, Agent, or Firm* — McDonnell Boehnen Hulbert & Berghoff LLP

(57) ABSTRACT

The present invention provides a dicistronic message for producing an antibody molecule, in which the upstream cistron contains DNA coding for the light chain of the antibody and the downstream cistron contains DNA coding for the corresponding heavy chain, characterised in that the dicistronic message comprises a sequence selected from AEOS1 (SEQ ID NO:1), AEOS2 (SEQ ID NO:2), AEOS3 (SEQ ID NO:3), AEOS4 (SEQ ID NO: 4), AEOS5 (SEQ ID NO:5), AEOS6 (SEQ ID NO:6), AEOS7 (SEQ ID NO:7), AEOS8 (SEQ ID NO:8), AEOS9 (SEQ ID NO:9), AEOS1O (SEQ ID NO:10) and AEOS11 (SEQ ID NO:11).

6 Claims, 15 Drawing Sheets

Figure 1. Antibody Expression Optimisation Sequences (AEOS)

| Name | Sequence | Stop-ATG | Notes/SEQ ID NO: |
|---|---|---|---|
| AEOS1 | R  G  E  C  *<br>AGG GGA GAG TGT TAA<br>ATGCATAATCATCAAAGGACTAGTGCTCTTCGGTC<br>                                M<br>GAGTTCTAGATAACGAGGCGTAAAAAATG | 62 | SEQ ID NO:1 |
| AEOS2 | R  G  E  C  *  M<br>AGA GGA GAG TGT TAAATG | 0 | SEQ ID NO:2 |
| AEOS3 | R  G  E  C  *  M<br>AGA GGA GAG TGT TAATAATG | +1 | SEQ ID NO:3 |
| AEOS4 | R  G  E  C  *  M<br>AGA GGA GAG TGT TAATAAATG | +2 | SEQ ID NO:4 |
| AEOS5 | R  G  E  C  *  M<br>AGA GGA GAG TGT TAATAAAATG | +3 | SEQ ID NO:5 |
| AEOS6 | R  G  E  C  *  M<br>AGA GGA GAG TGT TAATAAAAATG | +4 | SEQ ID NO:6 |
| AEOS7 | R  G  E  C  *  M<br>AGA GGA GAG TGT TAATAAAAAATG | +5 | SEQ ID NO:7 |
| AEOS8 | R  G  E  C  *  M<br>AGA GGA GAG TGT TAATAAAAAAATG | +6 | SEQ ID NO:8 |
| AEOS9 | R  G  E  C  *  M<br>AGA GGA GAG TGT TAATAATAAATG | +6 | SEQ ID NO:9 |
| AEOS10 | R  G  E  C  *  M<br>AGA GGA GAG TGT TAAAAAAAAATG | +6 | SEQ ID NO:10 |
| AEOS11 | R  G  E  C  *  M<br>AGA GGA GAG TGT TAAAAATG | +1 | SEQ ID NO:11 |

Figure 2. Cassettes containing Antibody expression optimisation sequences

| Name | Sequence | AEOS | Notes |
|---|---|---|---|
| IGS1 | S  F  N  R  G  E  C  *        M  K  K  T  A  I    I<br>A AGT TTT AAT AGA GGA GAG TGT TAATGAAGAAGACTGCTATAGCAATTG | N/A | WO03048208 |
| IGS2 | S  F  N  R  G  E  C  *      M  K  K  T  A  I    I<br>A AGT TTT AAT AGA GGG GAG TGT TAAAATGAAGAAGACTGCTATAGCAATTG | N/A | WO03048208 |
| IGS3 | S  F  N  R  G  E  C  *                                     M  K  K  T  A  I<br>A AGC TTT AAT AGA GGA GAG TGT TGAGGAGGAAAAAAAATGAAGAAAACTGCTATA<br>A  I<br>GCAATTG | N/A | WO03048208 |
| IGS4 | S  F  N  R  G  E  C  *                       M  K  K  T  A  I<br>A AGC TTT AAT AGA GGA GAG TGT TGA CGAGGATTATATAATGAAGAAAACTGCTATA<br>A  I<br>GCAATTG | N/A | WO03048208 |
| IGS5 | S  F  N  R  G  E  C  *<br>A AGC TTT AAT AGG GGA GAG TGT TAA ATGCATAATCATCAAAGGGACTAGTGCTCTT<br>CGGTCGAGTTCTAGATAACGAGGCGTAAAAAAATGAAAAAGACTGCTATAGCAATTG<br>                                M  K  K  T  A  I | 1 | SEQ ID NO: 12 |
| IGS7 | S  F  N  R  G  E  C  *        M  K  K  T  A  I  A  I<br>A AGC TTT AAT AGA GGA GAG TGT TAATGAAAAAGACTGCTATAGCAATTG | N/A | IGS1 of WO03048208 with altered restriction site and OmpA leader |
| IGS8 | S  F  N  R  G  E  C  *      M  K  K  T  A  I  A  I<br>A AGC TTT AAT AGA GGA GAG TGT TAAATGAAAAAGACTGCTATAGCAATTG | 2 | SEQ ID NO: 13 |
| IGS9 | S  F  N  R  G  E  C  *     M  K  K  T  A  I  A  I<br>A AGC TTT AAT AGA GGA GAG TGT TAATATGAAAAAGACTGCTATAGCAATTG | 3 | SEQ ID NO: 14 |
| IGS10 | S  F  N  R  G  E  C  *    M  K  K  T  A  I  A  I<br>A AGC TTT AAT AGA GGA GAG TGT TAATAATGAAAAAGACTGCTATAGCAATTG | 4 | SEQ ID NO: 15 |
| IGS11 | S  F  N  R  G  E  C  *   M  K  K  T  A  I  A  I<br>A AGC TTT AAT AGA GGA GAG TGT TAATAAATGAAAAAGACTGCTATAGCAATTG | 5 | SEQ ID NO: 16 |

Figure 2 continued.

| Name | Sequence | AEOS | Notes |
|---|---|---|---|
| IGS12 | S  F  N  R  G  E  C  *                M  K  K  T  A  I  A  I<br>A AGC TTT AAT AGA GGA GAG TGT TAATAAA*AT*GAAAAAGACTGCTATAGCAATTG | 6 | SEQ ID NO: 17 |
| IGS13 | S  F  N  R  G  E  C  *            M  K  K  T  A  I  A  I<br>A AGC TTT AAT AGA GGA GAG TGT TAATAAAA*AT*GAAAAAGACTGCTATAGCAATTG | 7 | SEQ ID NO: 18 |
| IGS14 | S  F  N  R  G  E  C  *            M  K  K  T  A  I  A  I<br>A AGC TTT AAT AGA GGA GAG TGT TAATAAAAA*AT*GAAAAAGACTGCTATAGCAATTG | 8 | SEQ ID NO: 19 |
| IGS15 | S  F  N  R  G  E  C  *           M  K  K  T  A  I  A  I<br>A AGC TTT AAT AGA GGA GAG TGT TAATAATAA*AT*GAAAAAGACTGCTATAGCAATTG | 9 | SEQ ID NO: 20 |
| IGS16 | S  F  N  R  G  E  C  *           M  K  K  T  A  I  A  I<br>A AGC TTT AAT AGA GGA GAG TGT TAAAAAAAA*AT*GAAAAAGACTGCTATAGCAATTG | 10 | SEQ ID NO: 21 |
| IGS17 | S  F  N  R  G  E  C  *           M  K  K  T  A  I  A  I<br>A AGC TTT AAT AGA GGA GAG TGT TAAAAA*AT*GAAGAAACTGCTATAGCAATTG | 11 | SEQ ID NO: 22 |
| IGS18 | S  F  N  R  G  E  C  *           M  K  K  T  A  I  A  I<br>A AGC TTT AAT AGA GGA GAG TGT TAATAA*AT*GAAGAAACTGCTATAGCAATTG | 4 | SEQ ID NO: 23 |

AAGCTT = *Hind*III site
CAATTG = *Mun*I site

Figure 8

VL kappa Amino acid seq.

diqmtqspsslsasvgdrvtitckasqnvgtnvawyqqkpgkapkaliysa
    sflysgvpyrfsgsgsgtdftltisslqpedfatyycqqyniypltfgqgt
    kveikrtvaapsvfifppsdeqlksgtasvvcllnnfypreakvqwkvdna
    lqsgnsqesvteqdskdstyslsstltlskadyekhkvyacevthqglssp
    vtksfnrgec

Figure 9

VH CH1 Amino acid seq.

evqlvesggglvqpggslrlscaasgyvftdygmnwvrqapgkglewmgwi
    ntyigepiyadsvkgrftfsldtskstaylqmnslraedtavyycargyrs
    yamdywgqgtlvtvssastkgpsvfplapsskstsggtaalgclvkdyfpe
    pvtvswnsgaltsgvhtfpavlqssglyslssvvtvpssslgtqtyicnvn
    hkpsntkvdkkvepkscdkthtcaa Figure 10
Complete coding region of anti-TNFα Fab' fragment comprising AEOS11 and OmpA leaders

```
atgaaaaagacagctatcgcaattgcagtggccttggctggtttcgctacc
gtagcgcaagctgacattcaaatgacccagagcccatccagcctgagcgca
tctgtaggagaccgggtcaccatcacttgtaaagccagtcagaacgtaggt
actaacgtagcctggtatcagcaaaaaccaggtaaagccccaaaagccctc
atctacagtgcctctttcctctatagtggtgtaccatacaggttcagcgga
tccggtagtggtactgatttcaccctcacgatcagtagcctccagccagaa
gatttcgccacttattactgtcaacagtataacatctacccactcacattc
ggtcagggtactaaagtagaaatcaaacgtacggtagcggcccatctgtc
ttcatcttcccgccatctgatgagcagttgaaatctggaactgcctctgtt
gtgtgcctgctgaataacttctatcccagagaggccaaagtacagtggaag
gtggataacgccctccaatcgggtaactcccaggagagtgtcacagagcag
gacagcaaggacagcacctacagcctcagcagcaccctgacgctgagcaaa
gcagactacgagaaacacaaagtctacgcctgcgaagtcacccatcagggc
ctgagctcaccagtaacaaaaagctttaatagaggagagtgttaaaatgaa
gaaaactgctatagcaattgcagtggcgctagctggtttcgccaccgtggc
gcaagctgaggttcagctggtcgagtcaggaggcggtctcgtgcagcctgg
cggatcactgagattgtcctgtgctgcatctggttacgtcttcacagacta
tggaatgaattgggttagacaggccccgggaaagggcctggaatggatggg
ttggattaatacttacattggagagcctatttatgctgacagcgtcaaggg
cagattcacgttctctctagacacatccaagtcaacagcatacctccaaat
gaatagcctgagagcagaggacaccgcagtgtactattgtgctagaggata
cagatcttatgccatggactactggggccagggtaccctagtcacagtctc
ctcagcttccaccaagggcccatcggtcttccccctggcaccctcctccaa
gagcacctctggggcacagcggccctgggctgcctggtcaaggactactt
ccccgaaccggtgacggtgtcgtggaactcaggcgccctgaccagcggcgt
gcacaccttcccggctgtcctacagtcctcaggactctactccctcagcag
cgtggtgaccgtgccctccagcagcttgggcacccagacctacatctgcaa
cgtgaatcacaagcccagcaacaccaaggtcgacaagaaagttgagcccaa
atcttgtgacaaaactcacacatgcgccgcgtgatga
```

FIGURE 11 (1 of 3)

Complete coding region plus translation of anti-TNFα Fab' fragment comprising AEOS11 and OmpA leaders.
(SEQ ID NOS: 26-28)

```
 M   K   K   T   A   I   A   I   A   V
ATG AAA AAG ACA GCT ATC GCA ATT GCA GTG
 A   L   A   G   F   A   T   V   A   Q
GCC TTG GCT GGT TTC GCT ACC GTA GCG CAA
 A   D   I   Q   M   T   Q   S   P   S
GCT GAC ATT CAA ATG ACC CAG AGC CCA TCC
 S   L   S   A   S   V   G   D   R   V
AGC CTG AGC GCA TCT GTA GGA GAC CGG GTC
 T   I   T   C   K   A   S   Q   N   V
ACC ATC ACT TGT AAA GCC AGT CAG AAC GTA
 G   T   N   V   A   W   Y   Q   Q   K
GGT ACT AAC GTA GCC TGG TAT CAG CAA AAA
 P   G   K   A   P   K   A   L   I   Y
CCA GGT AAA GCC CCA AAA GCC CTC ATC TAC
 S   A   S   F   L   Y   S   G   V   P
AGT GCC TCT TTC CTC TAT AGT GGT GTA CCA
 Y   R   F   S   G   S   G   S   G   T
TAC AGG TTC AGC GGA TCC GGT AGT GGT ACT
 D   F   T   L   T   I   S   S   L   Q
GAT TTC ACC CTC ACG ATC AGT AGC CTC CAG
 P   E   D   F   A   T   Y   Y   C   Q
CCA GAA GAT TTC GCC ACT TAT TAC TGT CAA
 Q   Y   N   I   Y   P   L   T   F   G
CAG TAT AAC ATC TAC CCA CTC ACA TTC GGT
 Q   G   T   K   V   E   I   K   R   T
CAG GGT ACT AAA GTA GAA ATC AAA CGT ACG
 V   A   A   P   S   V   F   I   F   P
GTA GCG GCC CCA TCT GTC TTC ATC TTC CCG
 P   S   D   E   Q   L   K   S   G   T
CCA TCT GAT GAG CAG TTG AAA TCT GGA ACT
 A   S   V   V   C   L   L   N   N   F
GCC TCT GTT GTG TGC CTG CTG AAT AAC TTC
 Y   P   R   E   A   K   V   Q   W   K
TAT CCC AGA GAG GCC AAA GTA CAG TGG AAG
 V   D   N   A   L   Q   S   G   N   S
GTG GAT AAC GCC CTC CAA TCG GGT AAC TCC
 Q   E   S   V   T   E   Q   D   S   K
CAG GAG AGT GTC ACA GAG CAG GAC AGC AAG
 D   S   T   Y   S   L   S   S   T   L
GAC AGC ACC TAC AGC CTC AGC AGC ACC CTG
```

FIGURE 11, cont'd (2 of 3)

```
 T   L   S   K   A   D   Y   E   K   H
ACG CTG AGC AAA GCA GAC TAC GAG AAA CAC
 K   V   Y   A   C   E   V   T   H   Q
AAA GTC TAC GCC TGC GAA GTC ACC CAT CAG
 G   L   S   S   P   V   T   K   S   F
GGC CTG AGC TCA CCA GTA ACA AAA AGC TTT

N   R   G   E   C   *
AAT AGA GGA GAG TGT TAA A
                             M   K   K
                            ATG AAG AAA
 T   A   I   A   I   A   V   A   L   A
ACT GCT ATA GCA ATT GCA GTG GCG CTA GCT
 G   F   A   T   V   A   Q   A   E   V
GGT TTC GCC ACC GTG GCG CAA GCT GAG GTT
 Q   L   V   E   S   G   G   G   L   V
CAG CTG GTC GAG TCA GGA GGC GGT CTC GTG
 Q   P   G   G   S   L   R   L   S   C
CAG CCT GGC GGA TCA CTG AGA TTG TCC TGT
 A   A   S   G   Y   V   F   T   D   Y
GCT GCA TCT GGT TAC GTC TTC ACA GAC TAT
 G   M   N   W   V   R   Q   A   P   G
GGA ATG AAT TGG GTT AGA CAG GCC CCG GGA
 K   G   L   E   W   M   G   W   I   N
AAG GGC CTG GAA TGG ATG GGT TGG ATT AAT
 T   Y   I   G   E   P   I   Y   A   D
ACT TAC ATT GGA GAG CCT ATT TAT GCT GAC
 S   V   K   G   R   F   T   F   S   L
AGC GTC AAG GGC AGA TTC ACG TTC TCT CTA
 D   T   S   K   S   T   A   Y   L   Q
GAC ACA TCC AAG TCA ACA GCA TAC CTC CAA
 M   N   S   L   R   A   E   D   T   A
ATG AAT AGC CTG AGA GCA GAG GAC ACC GCA
 V   Y   Y   C   A   R   G   Y   R   S
GTG TAC TAT TGT GCT AGA GGA TAC AGA TCT
 Y   A   M   D   Y   W   G   Q   G   T
TAT GCC ATG GAC TAC TGG GGC CAG GGT ACC
 L   V   T   V   S   S   A   S   T   K
CTA GTC ACA GTC TCC TCA GCT TCC ACC AAG
 G   P   S   V   F   P   L   A   P   S
GGC CCA TCG GTC TTC CCC CTG GCA CCC TCC
 S   K   S   T   S   G   G   T   A   A
TCC AAG AGC ACC TCT GGG GGC ACA GCG GCC
```

FIGURE 11, cont'd (3 of 3)

```
 L   G   C   L   V   K   D   Y   F   P
CTG GGC TGC CTG GTC AAG GAC TAC TTC CCC
 E   P   V   T   V   S   W   N   S   G
GAA CCG GTG ACG GTG TCG TGG AAC TCA GGC
 A   L   T   S   G   V   H   T   F   P
GCC CTG ACC AGC GGC GTG CAC ACC TTC CCG
 A   V   L   Q   S   S   G   L   Y   S
GCT GTC CTA CAG TCC TCA GGA CTC TAC TCC
 L   S   S   V   V   T   V   P   S   S
CTC AGC AGC GTG GTG ACC GTG CCC TCC AGC
 S   L   G   T   Q   T   Y   I   C   N
AGC TTG GGC ACC CAG ACC TAC ATC TGC AAC
 V   N   H   K   P   S   N   T   K   V
GTG AAT CAC AAG CCC AGC AAC ACC AAG GTC
 D   K   K   V   E   P   K   S   C   D
GAC AAG AAA GTT GAG CCC AAA TCT TGT GAC
 K   T   H   T   C   A   A   *   *
AAA ACT CAC ACA TGC GCC GCG TGA TGA
```

EXPRESSION CONTROL USING ANTIBODY EXPRESSION OPTIMISATION SEQUENCES

This is a National Stage of International Application No. PCT/GB06/003640, filed Sep. 29, 2006, which claims priority to GB application No. 0520169.4, filed on Oct. 4, 2005.

The present invention relates to methods of producing antibodies wherein the heavy and light chains of a particular antibody molecule are encoded by the DNA present in a dicistronic message. More specifically the present invention provides a suite of sequences for optimising antibody expression and yield when the antibody is expressed as a dicistronic message.

WO03/048208 describes specific dicistronic messages which can be used for optimising the expression and yield of antibodies.

The present invention provides a suite of 11 antibody expression optimisation sequences (AEOS) which can be used to improve the expression and yield of antibodies when the antibodies are expressed as a dicistronic message. Accordingly, the present invention provides a dicistronic message for producing an antibody molecule, in which the upstream cistron contains DNA coding for the light chain of the antibody and the downstream cistron contains DNA coding for the corresponding heavy chain, characterised in that the dicistronic message comprises a sequence selected from AEOS1 (SEQ ID NO: 1), AEOS2 (SEQ ID NO: 2), AEOS3 (SEQ ID NO:3), AEOS4 (SEQ ID NO: 4), AEOS5 (SEQ ID NO:5), AEOS6 (SEQ ID NO:6), AEOS7 (SEQ ID NO:7), AEOS8 (SEQ ID NO:8), AEOS9 (SEQ ID NO:9), AEOS10 (SEQ ID NO:10) and AEOS11 (SEQ ID NO:11).

The dicistronic message of the present invention codes for the heavy chain and the light chain of a particular antibody molecule. The antibody of the present invention may be any heavy chain and light chain pair having a variable ($V_H/V_L$) and constant region ($C_H/C_L$) where the light chain constant region of the antibody is preferably the kappa isotype. The antibody may be a whole antibody or in particular a fragment thereof such as a Fab or a Fab' or a truncated Fab fragment as described in WO2005/003170.

Fab' fragments of the present invention may possess a native or a modified hinge region. The native hinge region is the hinge region normally associated with the $C_H1$ domain of the antibody molecule. A modified hinge region is any hinge that differs in length and/or composition from the native hinge region. Such hinges can include hinge regions from any suitable species, such as human, mouse, rat, rabbit, pig, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as alanine, or by converting suitably placed residues into cysteine residues. By such means the number of cysteine residues in the hinge region may be increased or decreased. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerization properties. Other modified hinge regions may be entirely synthetic and may be designed to possess desired properties such as length, composition and flexibility. A number of modified hinge regions have already been described for example, in U.S. Pat. No. 5,677,425, WO99/15549, WO98/25971 and WO2005/003171 and these are incorporated herein by reference.

The antibody of the present invention may be derived from any antibody isotype including for example IgG, IgM, IgA, IgD and IgE and subclasses thereof including for example IgG1, IgG2, IgG3 and IgG4. Preferably the antibody of the present invention is derived from IgG1. Preferably the light chain constant region is the kappa isotype. The antibody may be obtained from any species including for example mouse, rat, rabbit, pig, hamster, camel, llama, goat or human. Preferably at least the constant regions of the antibody of the present invention are human. Parts of the antibody may be obtained from more than one species for example the antibodies may be chimeric. In one example the constant regions are from one species and the variable regions are from another. In another example the variable region of the antibody has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The methods for creating and manufacturing recombinant antibodies are well known in the art (see for example, Boss et al., U.S. Pat. No. 4,816,397; Cabilly et al., U.S. Pat. No. 6,331,415; Shrader et al., WO 92/02551; Orlandi et al., 1989, Proc. Natl. Acad. Sci. USA, 86, 3833; Riechmann et al., 1988, Nature, 322, 323; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

The antibody molecule of the present invention will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

The dicistronic message of the present invention may comprise synthetic DNA, cDNA or genomic DNA, or any combination thereof.

The coding DNA sequence for a particular antibody can be obtained by methods well known to those skilled in the art. For example, DNA sequences coding for part or all of the antibody heavy and light chains may be synthesised as desired from the determined DNA sequences or on the basis of the corresponding amino acid sequences.

Standard techniques of molecular biology may be used to prepare DNA sequences coding for the heavy and light chains of specific antibody molecules and comprising the sequences provided by the present invention. Desired DNA sequences may be synthesised completely or in part using oligonucleotide synthesis techniques. Site-directed mutagenesis and polymerase chain reaction (PCR) techniques may be used as appropriate.

The dicistronic message of the present invention may contain a DNA sequence encoding an effector or reporter protein that is fused to the DNA sequence encoding one of the antibody chains.

The dicistronic message of the present invention may also contain a DNA sequence encoding a peptide linkage which is fused to the DNA sequence encoding one of the antibody chains such that it will allow the subsequent attachment of an effector or reporter protein or molecule to the antibody expressed from the discistronic message.

The dicistronic message of the present invention may also contain a secretory signal sequence that is fused upstream of the DNA sequence encoding one or both of the antibody chains in order to allow targeting of the antibody chains to the periplasm or to outside the cell.

Preferably, the secretory signal sequence is an OmpA peptide sequence. Preferably the secretory signal sequence for both the heavy and the light chain is the OmpA peptide sequence.

Preferably the antibody molecule encoded by the dicistronic message of the present invention is an anti-tumour necrosis factor-α antibody. Even more preferably the antibody molecule encoded by the dicistronic message of the present invention has a specificity for human TNFα and comprises a light chain consisting of the sequence given in FIG. 8 (SEQ ID NO:24) and a heavy chain consisting of the sequence given in FIG. 9 (SEQ ID NO:25). Preferably where the antibody encoded by the dicistronic message is an anti-TNF-α antibody Fab' fragment the dicistronic message comprises the sequence AEOS11 (SEQ ID NO:11). In one embodiment where the antibody encoded by the dicistronic message is an anti-TNF-α antibody Fab' fragment the dicistronic message comprises the sequence of IGS 17 (SEQ ID NO:22). In one preferred embodiment the dicistronic message of the present invention comprises the sequence provided in FIG. 10 (SEQ ID NO:26).

The antibody expression optimisation sequences of the present invention have been modified with respect to length, sequence and secondary structure such that improved translational coupling of the two cistrons is achieved.

As described in WO03/048208 there are several features of dicistronic messages which can influence translation of the downstream cistron. These include the presence of a Shine-Dalgarno (SD) motif in the upstream cistron, the nature of the SD motif, the distance between the SD site and the AUG start codon of the downstream cistron, the distance between the stop codon of the upstream cistron and the AUG start codon of the downstream cistron and the nature of this intervening sequence.

The AEO sequences of the present invention all encompass a Shine-Dalgano (SD) motif (ribosome binding site) and a specific range of nucleotide distances from this to the initiator (start) codon of the $2^{nd}$ of the two genes in the dicistron. In contrast to previously described sequences (See WO03/048208) a uniform SD and stop codon were used in each of the sequences to optimise expression levels for the second gene in the cistron.

The AEO nucleotide sequences provided by the present invention are AEOS1 (SEQ ID NO: 1), AEOS2 (SEQ ID NO: 2), AEOS3 (SEQ ID NO:3), AEOS4 (SEQ ID NO: 4), AEOS5 (SEQ ID NO:5), AEOS6 (SEQ ID NO:6), AEOS7 (SEQ ID NO:7), AEOS8 (SEQ ID NO:8), AEOS9 (SEQ ID NO:9), AEOS10 (SEQ ID NO:10) and AEOS11 (SEQ ID NO:11) as shown in FIG. 1.

Sequence shown includes:
i) 3' 12 bp of human cKappa (encoding $^N$RGEC$^C$)
ii) internal Shine-Dalgarno site (underlined)
iii) TAA stop codon (*) and intergenic sequence spacer between stop codon and start codon ATG.
iv) start codon ATG Also indicated is the distance between the stop codon of the first cistron and the ATG of the second cistron.

It will be appreciated that the start codon ATG may be replaced by other suitable codons such as GTG and TTG.

The optimal antibody expression optimization sequence for a given antibody molecule can be empirically determined using the following method. The method comprises constructing a series of suitable expression vectors containing a series of AEO sequence variants selected from AEOS1 (SEQ ID NO: 1), AEOS2 (SEQ ID NO: 2), AEOS3 (SEQ ID NO:3), AEOS4 (SEQ ID NO: 4), AEOS5 (SEQ ID NO:5), AEOS6 (SEQ ID NO:6), AEOS7 (SEQ ID NO:7), AEOS8 (SEQ ID NO:8), AEOS9 (SEQ ID NO:9), AEOS10 (SEQ ID NO:10) and AEOS11 (SEQ ID NO:11) into which antibody molecules can be inserted for testing. Empirical testing of each AEO sequence for each antibody can be achieved by transforming the expression vector into a suitable host and analysing antibody expression and yield. The suite of AEO sequences described in the present application, which vary in length and sequence, can be used to construct such vectors from which the optimal AEO sequence for a particular antibody molecule can be selected. Also provided by the present invention are a suite of DNA cassettes containing each of the AEO sequences in which uniform restriction sites are used to facilitate clone construction (FIG. 2). These cassettes comprise a HindIII and a MunI restriction site which are suitable for insertion of the light chain and the heavy chain of the antibody molecule respectively, where the heavy chain sequence is preceded by the OmpA leader sequence. These cassettes comprise the C-terminus of the light chain constant region, cKappa, in the first cistron (SFNRGEC) and part of the N-terminus of the OmpA leader sequence in the second cistron (MKKTAIAI). The cassette sequences provided by the present invention are IGS5 (SEQ ID NO:12), IGS8 (SEQ ID NO:13), IGS9 (SEQ ID NO:14), IGS10 (SEQ ID NO:15), IGS11 (SEQ ID NO:16), IGS12 (SEQ ID NO:17), IGS13 (SEQ ID NO:18), IGS14 (SEQ ID NO:19), IGS15 (SEQ ID NO:20), IGS16 (SEQ ID NO:21), IGS17 (SEQ ID NO:22) and IGS18 (SEQ ID NO:23).

Accordingly, the invention also provides an expression vector containing the dicistronic message of the present invention.

Suitable expression vectors are well known in the art. Examples of such vectors include pTTO and pTTOD as described in WO03/048208.

The present invention also provides a cloning vector containing a dicistronic message according to the present invention.

General methods by which the expression and cloning vectors may be constructed, transformation methods and culture methods are well known to those skilled in the art.

The present invention also provides a process for the production of a particular antibody molecule comprising culturing a bacterial host cell that has been transformed with an expression vector of the present invention under conditions suitable for leading to expression of DNA encoding said antibody molecule, and isolating said antibody molecule, wherein the expression level of said antibody has been optimised.

Any suitable bacterial host cell may be used for expression of the heavy and light chains of the particular antibody molecule encoded by a dicistronic message according to the present invention. Preferably the bacterial host cell is gram negative, including but not limited to *Salmonella, Erwinia* and *E. coli*. Preferably *E. coli* host cells are used. Other microbial systems may also be used.

The antibody molecule may be secreted outside of the cell or targeted to the periplasm by suitable signal sequences. Alternatively, the antibody molecules may accumulate within the cell's cytoplasm. Depending on the antibody being produced and the process used, it may be desirable to allow the antibody molecule to refold and form a functional conformation. Procedures for allowing the antibody molecule to refold are well known to those skilled in the art.

The antibody molecules of the present invention, once produced in a host cell may be extracted and purified using any suitable method known in the art. Suitable purification methods include but are not limited to size exclusion, hydrophobic interaction chromatography, protein A, G or L affinity chromatography and ion exchange.

The antibody molecules produced by a dicistronic message according to the present invention may be used to make a therapeutic or diagnostic composition comprising a particular antibody in combination with a pharmaceutically acceptable excipient, diluent or carrier.

The antibody molecule may be the sole active ingredient in the therapeutic or diagnostic composition or may be accompanied by one or more other active ingredients including other antibody ingredients, for example, anti-T cell, anti-IFNγ or anti-LPS antibodies, or non-antibody ingredients such as xanthines.

The particular antibody molecule produced by the present invention may be administered in any appropriate form and amount according to the therapy in which it is employed.

Suitable forms for administration include forms suitable for parenteral administration, e.g. by injection or infusion, for example, by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents.

Alternatively, the antibody molecule may be in dry form, for reconstitution before use with an appropriate sterile liquid.

If the antibody molecule is suitable for oral administration, for example in the case of antibody fragments, the formulation may contain, in addition to the active ingredient, suitable additives used in the formulation of orally administered compositions.

The therapeutic and diagnostic compositions may be in unit dosage form, in which case each unit dose comprises an effective amount of the particular antibody molecule. The dose will also be selected according to the age and condition of the patient.

If the antibody molecule has a short half life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The present invention is further described by way of illustration only in the following examples which refer to the accompanying drawings in which:

FIG. 1 shows Antibody Expression Optimisation Sequences (AEOS) for use in the present invention.

FIG. 2 shows cassettes containing antibody expression optimisation sequences.

FIG. 8 shows the amino acid sequence of the light chain of an anti-TNFα Fab' fragment.

FIG. 9 shows the amino acid sequence of the heavy chain of an anti-TNFα Fab' fragment.

FIG. 10 shows the complete coding region of an anti-TNFα Fab' fragment comprising AEOS11 and OmpA leaders FIG. 11 shows the complete coding region plus translation of an anti-TNFα Fab' fragment comprising AEOS11.

EXAMPLES

General Methods

A Dicistronic Message Encoding an Anti-TNFα Antibody

A dicistronic message of the present invention was used to achieve high level expression of the anti-TNFα Fab' fragment described in WO01/94585. The upstream cistron encoded the light chain of the antibody (FIG. 8) whilst the downstream cistron encoded the heavy chain of the antibody (FIG. 9). A DNA sequence encoding the OmpA signal peptide was fused to the 5' end of the DNA coding for each of the light chain and the heavy chain to allow efficient secretion to the periplasm.

A series of oligonucleotide cassettes coding for a range of different antibody expression optimisation sequences (AEOS) (FIG. 2) were used in the dicistronic message in order to vary the level of expression of the heavy chain. The use of different AEOSs altered the rate of translational initiation of the heavy chain, resulting in a range of rates of accumulation of the translated heavy chain product.

Methods were essentially as described in WO03/048208. IGS1, 2, 3 and 4 are from WO03/048208.

Constructs were made using long forward 5' oligos that spanned from the 5' HindIII site through to OmpA. Expression experiments were standard methods: transformation of plasmid into W3110, and the 200 ml LB 30° C. shake flask experiments in 2l flasks, induction at $OD_{600}$=0.5 with 200 µM IPTG. Time point samples were resuspended to 30 $OD_{600}$/ml in Tris/EDTA extraction buffer (100 mM/10 mM pH7.4) before shaking overnight at 30° C. Fab' concentration was assayed by assembly ELISA using 6045 capture (anti-CH1) and reveal with anti human-Kappa HRP conjugate (Southern Biotech HP6062).

Figure 3:
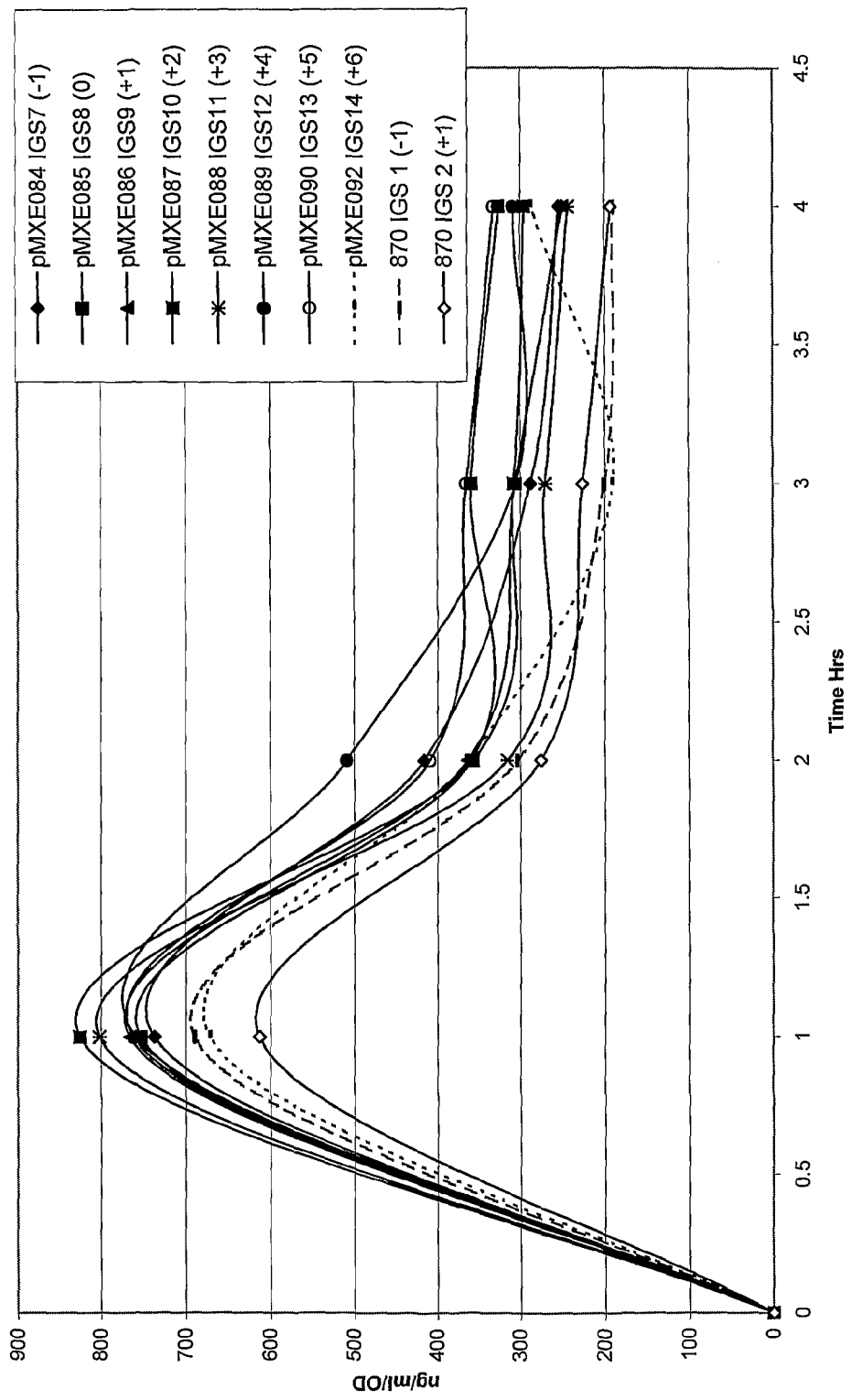
FIG. 3 shows a Fab' expression time course conducted in shake flasks in which IGS 7-14 were compared to the previously described IGS1 and IGS2.

An expression time course showed that IGS 7-14 were all capable of Fab' expression at levels equivalent to or better than the previously described IGS1 and IGS2 (FIG. 3). IGS 9 produced an increased yield compared to IGS2 even though they both have the same spacing between stop and start codons (+1); they differ in the presence/absence of HindIII site, spacing nucleotide A vs T and the first two lysine codons of OmpAII AAG AAG vs AAA AAG.

Figure 4:
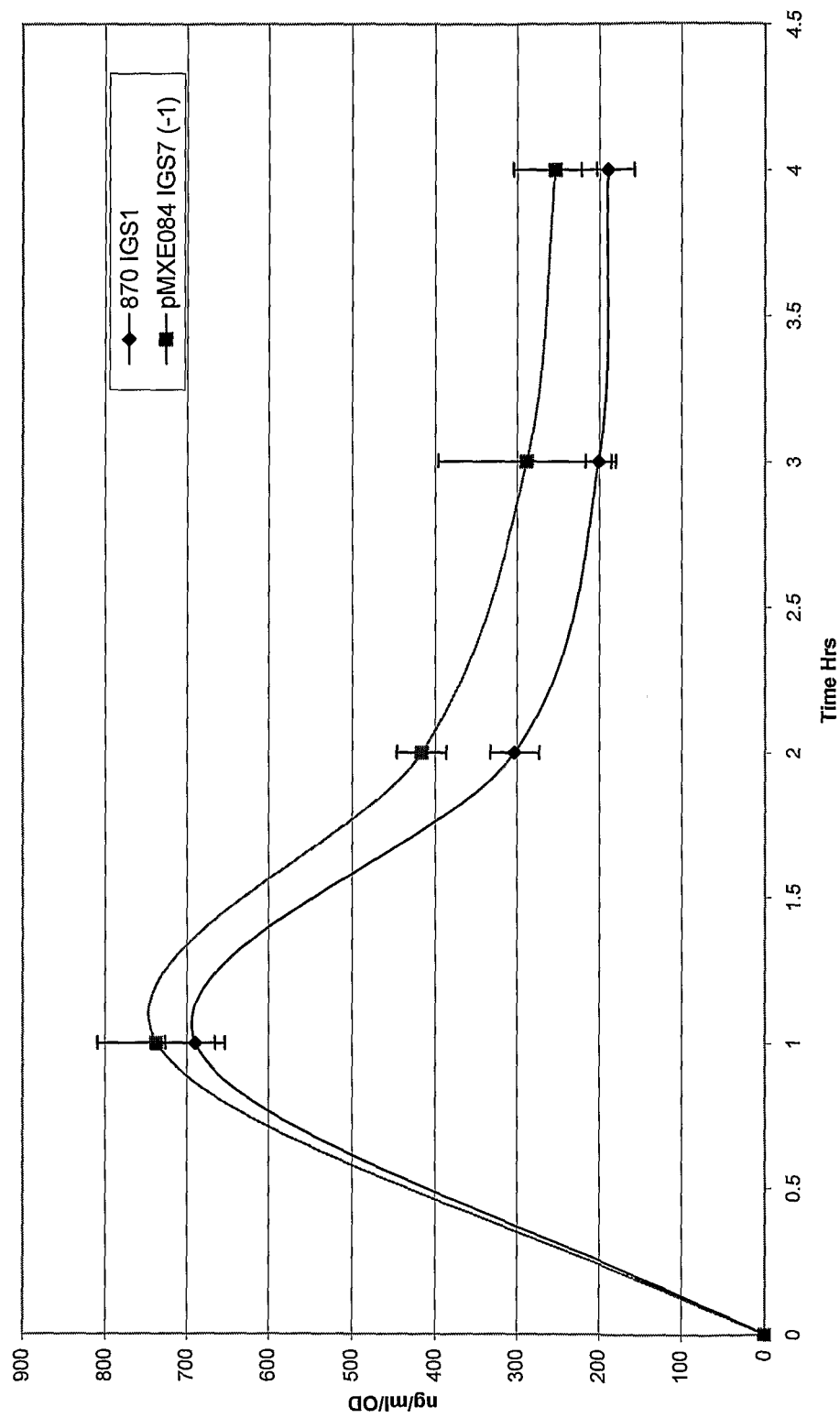
FIG. 4 shows a Fab' expression time course conducted in shake flasks in which the two IGS cassettes that both have an intergenic spacing of −1 (IGS1 and IGS7) were compared.
Figure 5A:
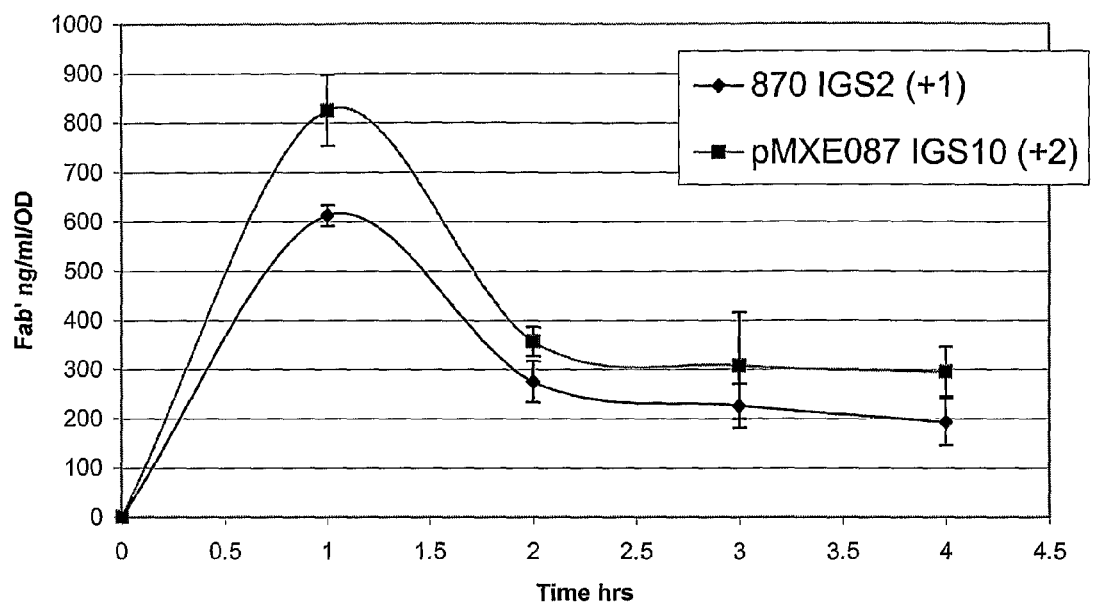
FIG. 5a shows a Fab' expression time course conducted in shake flasks in which IGS2 and IGS10 were compared.
Figure 5B:
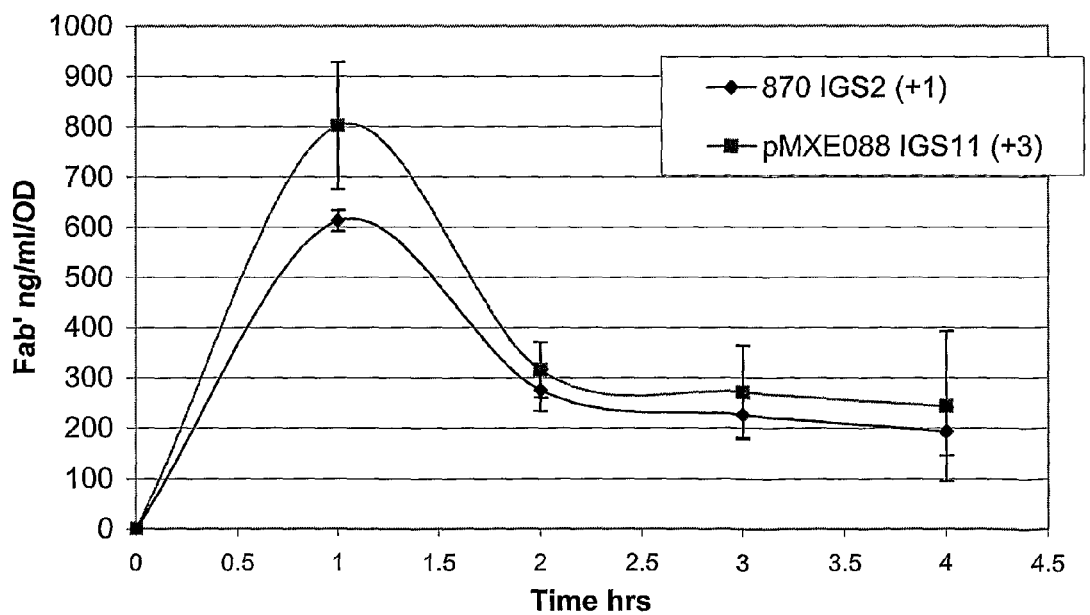
FIG. 5b shows a Fab' expression time course conducted in shake flasks in which IGS2 and IGS11 were compared.
Figure 5C:
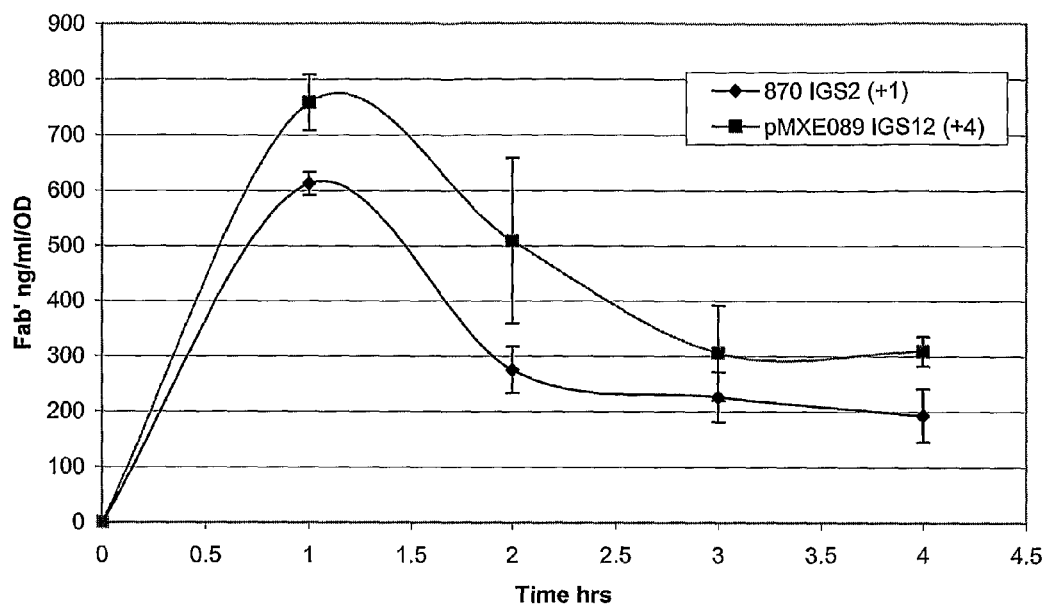
FIG. 5c shows a Fab' expression time course conducted in shake flasks in which IGS2 and IGS12 were compared.
Figure 5D:
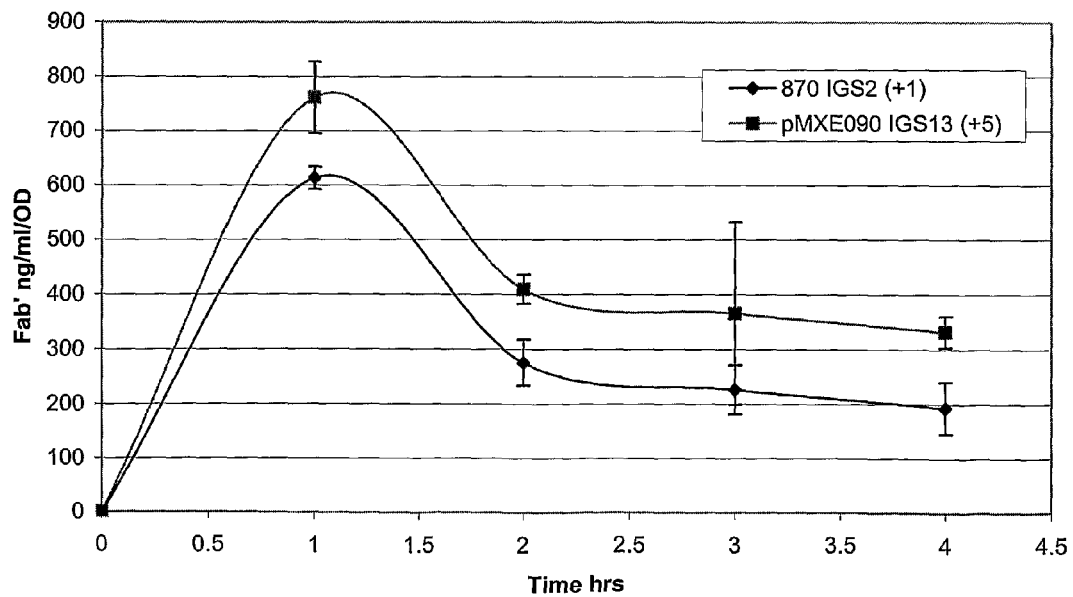
FIG. 5d shows a Fab' expression time course conducted in shake flasks in which IGS2 and IGS13 were compared.
Figure 5E:
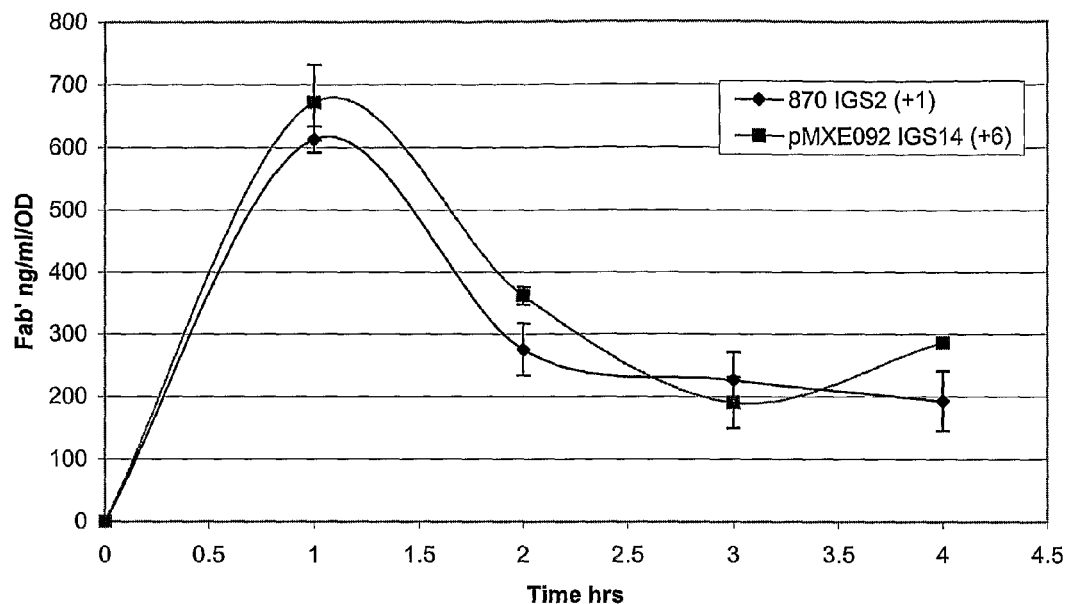
FIG. 5e shows a Fab' expression time course conducted in shake flasks in which IGS2 and IGS14 were compared.

FIG. 4 compares the two IGS plasmids that both have an intergenic spacing of −1 (IGS1 and IGS7). The Fab' expression from these plasmids is not significantly different suggesting that the presence of the HindIII site and change of the two lysine codons of OmpAII AAG AAG to AAA AAG does not result in a change in expression levels. Hence these two alterations also present in other IGS constructs can most likely be ignored when making comparisons between different IGS's. Hence in the following examples it is the AEO sequence which is of importance.

FIG. 5a-e: Comparison of IGS2 (spacing +1) against IGS10-13 (spacings of +2, +3, +4 and +5) demonstrates that the improvements in yield over that of IGS2 are due two factors: use of the GAGGAG SD sequence rather than the GAGGGG sequence used in IGS2 and having an optimal distance between the SD and the ATG start codon. Data suggest that the spacing of +2 and +3 are the best for this Fab', with a trend toward a steady reduction in yield with spacings of +4 and +5. This trend is supported by a further reduction in yield with IGS14 (+6) such that it has approximate equality of yield with IGS2 (+1), shown in FIG. 5e.

Figure 6:
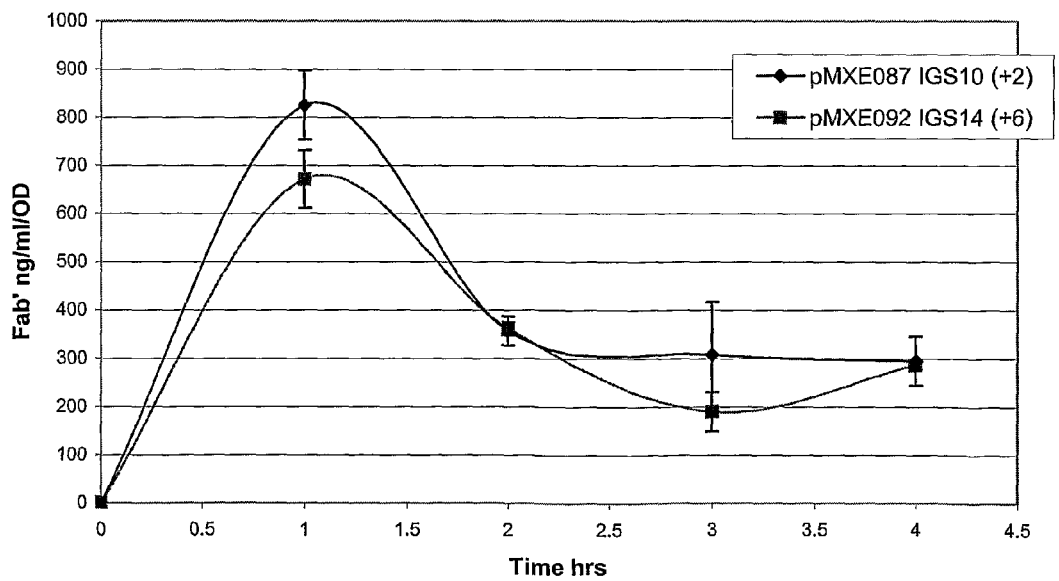
FIG. 6 shows a Fab' expression time course conducted in shake flasks in which IGS10 and IGS14 were compared.

FIG. 6 confirms that there is a significant difference between two plasmids where the only difference between the constructs is the spacing between the stop codon and ATG. IGS10 (+2) and IGS14 (+6) have identical HindIII, SD sequence, TAA stop codon and OmpAII codons of AAA AAG. This data confirms that the expression level of the second gene in a polycistron can be fine tuned by the length of SD-ATG spacing in an IGS and is therefore dependent on the AEO sequence in the IGS cassette.

The growth profiles of the new IGS cassettes 7-14 were tested and compared to IGS1 and IGS2. Cultures are induced when they reach an $OD_{600}$ of 0.5 and then followed for another 4 hours. Most of the cultures were observed to be similar with two notable exceptions. The plasmid encoding IGS9 (+1) enables the cells to grow to a higher $OD_{600}$ and continue growing better after induction than the other IGS cassettes. The next best growth profile is the plasmid encoding IGS2 (+1). The only common feature that these two IGS's have is the spacing gap of +1 residues. IGS2 and 9 are ±HindIII, GAGGGG vs GAGGAG, have A vs T between TAA and ATG and have AAG AAG vs AAA AAG lysine codons respectively. Since the yield of the IGS9 is somewhat higher than the IGS2 this growth advantage is unlikely to be due to reduced stress due to making less protein product. Hence, these data suggest that there is a biological advantage in the stop-ATG spacing of +1 conferred by benefits to the transcription/translation machinery.

Figure 7A:
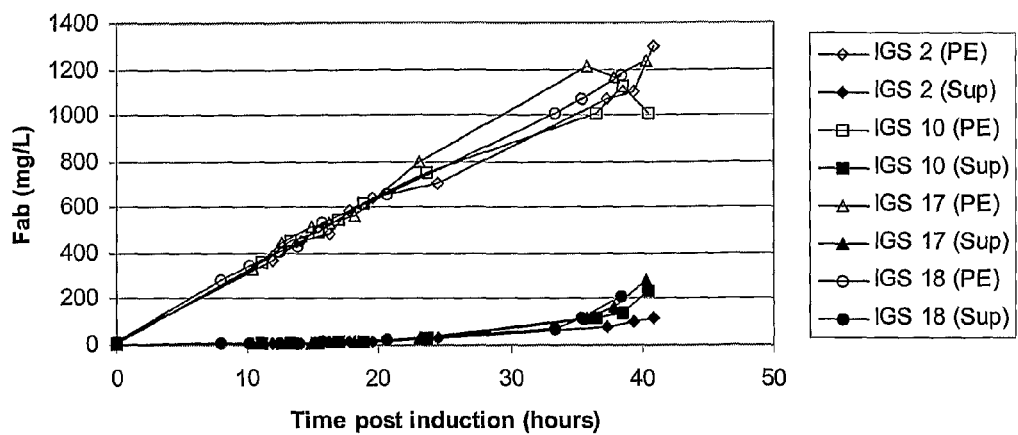
FIG. 7a shows a Fab' accumulation time course for periplasmic Fab' and media supernatant Fab' in a 1 litre fermentation using IGS 2, IGS 10, IGS 17 and IGS 18.
Figure 7B:
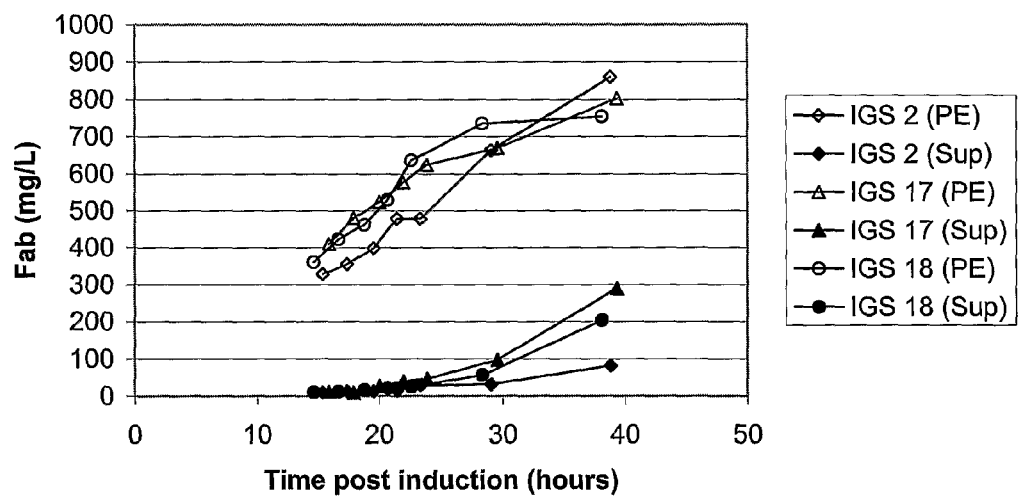
FIG. 7b shows a Fab' accumulation time course for periplasmic Fab' and media supernatant Fab' in a 1 litre fermentation using IGS 2, IGS 17 and IGS 18.
Figure 7C:
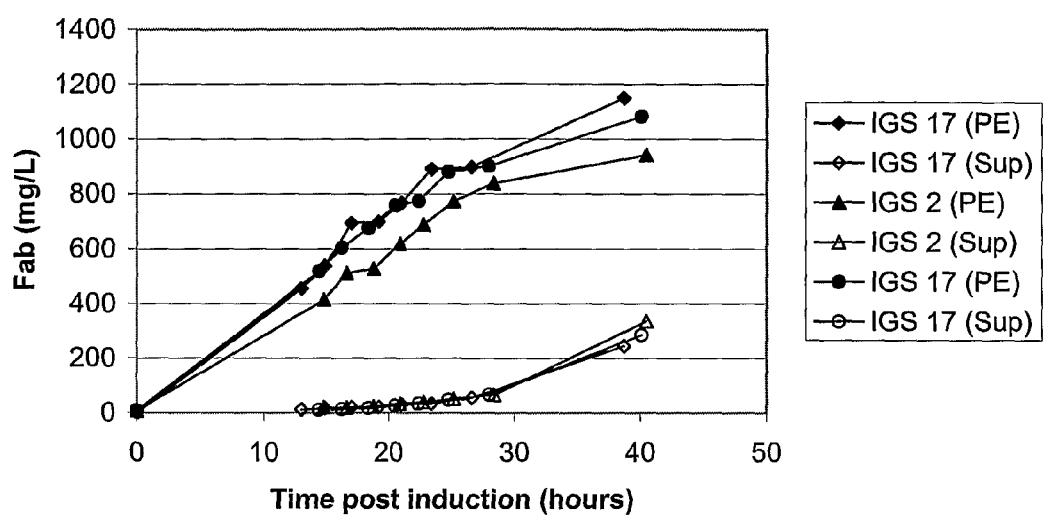
FIG. 7c shows a Fab' accumulation time course for periplasmic Fab' and media supernatant Fab' in a 1 litre fermentation using IGS 2 and IGS 17.

The growth profiles for various 1 liter fermentation test expression comparisons of IGS2 against IGS10, 17 and 18 showed that the new IGS's do not have a detrimental affect on *E. coli* growth pre or post Fab' induction. FIGS. 7a, b and c show the Fab' accumulation profiles for periplasmic material (measured by proteinG HPLC assay) and media supernatant material (measured by Fab' sandwich ELISA). Data show that the Fab' yield for IGS17 and 18 is not reduced when compared with IGS2. Fermentation data is necessarily prone to noise caused by sampling and assay variations but taken together the three sets of fermentation data suggest that IGS17 has improved Fab yield by some 10-20%.

The dicistronic message encoding the anti-TNFα antibody Fab' fragment which comprises IGS17 is given in FIG. 10 and the translation of this sequence is shown in FIG. 11.

The invention claimed is:

1. A dicistronic message for producing an a recombinant antibody molecule, in which the upstream cistron contains DNA coding for the light chain of the recombinant antibody and the downstream cistron contains DNA coding for the corresponding heavy chain, characterised in that the two cistrons are linked by an intergenic sequence (IGS), wherein the IGS is selected from IGS5 (SEQ ID NO: 12), IGS8 (SEQ ID NO: 13), IGS9 (SEQ ID NO:14), IGS10 (SEQ ID NO:15), IGS11 (SEQ ID NO:16), IGS12 (SEQ ID NO:17), IGS 13 (SEQ ID NO:18), IGS14 (SEQ ID NO: 19), IGS15 (SEQ ID NO:20), IGS16 (SEQ ID NO:21), IGS17 (SEQ ID NO:22) and IGS18 (SEQ ID NO:23).

2. The dicistronic message according to claim 1 in which the light chain of the recombinant antibody molecule encoded by the message comprises the sequence given in SEQ ID NO:24 and the heavy chain of the recombinant antibody molecule encoded by the message comprises the sequence given in SEQ ID NO:25.

3. The dicistronic message according to claim 2 in which the message comprises the sequence given in SEQ ID NO:26.

4. An isolated expression vector containing a dicistronic message according to claim 1.

5. An isolated expression vector according to claim 4, wherein the expression vector is pTTO-1.

6. An isolated host cell that has been transformed with an expression vector according to claim 4.

* * * * *

SEQUENCE LISTING

```
<160> NUMBER OF SEQ ID NOS: 28

<210> SEQ ID NO 1
<211> LENGTH: 80
<212> TYPE: DNA
<213> ORGANISM: Artificial
<220> FEATURE:
<223> OTHER INFORMATION: Synthetic; Polynucleotide for AEOS1

<400> SEQUENCE: 1
aggggagagt gttaaatgca taatcatcaa agggactagt gctcttcggt cgagttctag      60
ataacgaggc gtaaaaaatg                                                  80

<210> SEQ ID NO 2
<211> LENGTH: 18
<212> TYPE: DNA
<213> ORGANISM: Artificial
<220> FEATURE:
```

-continued

<223> OTHER INFORMATION: Synthetic; Polynucleotide for AEOS2

<400> SEQUENCE: 2
agaggagagt gttaaatg                     18

<210> SEQ ID NO 3
<211> LENGTH: 19
<212> TYPE: DNA
<213> ORGANISM: Artificial
<220> FEATURE:
<223> OTHER INFORMATION: Synthetic; Polynucleotide for AEOS3

<400> SEQUENCE: 3
agaggagagt gttaatatg                    19

<210> SEQ ID NO 4
<211> LENGTH: 20
<212> TYPE: DNA
<213> ORGANISM: Artificial
<220> FEATURE:
<223> OTHER INFORMATION: Synthetic; Polynucleotide for AEOS4

<400> SEQUENCE: 4
agaggagagt gttaataatg                   20

<210> SEQ ID NO 5
<211> LENGTH: 21
<212> TYPE: DNA
<213> ORGANISM: Artificial
<220> FEATURE:
<223> OTHER INFORMATION: Synthetic; Polynucleotide for AEOS5

<400> SEQUENCE: 5
agaggagagt gttaataaat g                 21

<210> SEQ ID NO 6
<211> LENGTH: 22
<212> TYPE: DNA
<213> ORGANISM: Artificial
<220> FEATURE:
<223> OTHER INFORMATION: Synthetic; Polynucleotide for AEOS6

<400> SEQUENCE: 6
agaggagagt gttaataaaa tg                22

<210> SEQ ID NO 7
<211> LENGTH: 23
<212> TYPE: DNA
<213> ORGANISM: Artificial
<220> FEATURE:
<223> OTHER INFORMATION: Synthetic; Polynucleotide for AEOS7

<400> SEQUENCE: 7
agaggagagt gttaataaaa atg               23

<210> SEQ ID NO 8
<211> LENGTH: 24
<212> TYPE: DNA
<213> ORGANISM: Artificial
<220> FEATURE:
<223> OTHER INFORMATION: Synthetic; Polynucleotide for AEOS8

<400> SEQUENCE: 8
agaggagagt gttaataaaa aatg              24

<210> SEQ ID NO 9

```
<211> LENGTH: 24
<212> TYPE: DNA
<213> ORGANISM: Artificial
<220> FEATURE:
<223> OTHER INFORMATION: Synthetic; Polynucleotide for AEOS9

<400> SEQUENCE: 9
agaggagagt gttaataata aatg                                              24

<210> SEQ ID NO 10
<211> LENGTH: 24
<212> TYPE: DNA
<213> ORGANISM: Artificial
<220> FEATURE:
<223> OTHER INFORMATION: Synthetic; Polynucleotide for AEOS10

<400> SEQUENCE: 10
agaggagagt gttaaaaaaa aatg                                              24

<210> SEQ ID NO 11
<211> LENGTH: 19
<212> TYPE: DNA
<213> ORGANISM: Artificial
<220> FEATURE:
<223> OTHER INFORMATION: Synthetic; Polynucleotide for AEOS11

<400> SEQUENCE: 11
agaggagagt gttaaaatg                                                    19

<210> SEQ ID NO 12
<211> LENGTH: 112
<212> TYPE: DNA
<213> ORGANISM: Artificial
<220> FEATURE:
<223> OTHER INFORMATION: Synthetic; Polynucleotide for IGS5

<400> SEQUENCE: 12
aagctttaat agggagagt gttaaatgca taatcatcaa agggactagt gctcttcggt        60
cgagttctag ataacgaggc gtaaaaaatg aaaaagactg ctatagcaat tg              112

<210> SEQ ID NO 13
<211> LENGTH: 50
<212> TYPE: DNA
<213> ORGANISM: Artificial
<220> FEATURE:
<223> OTHER INFORMATION: Synthetic; Polynucleotide for IGS8

<400> SEQUENCE: 13
aagctttaat agaggagagt gttaaatgaa aaagactgct atagcaattg                  50

<210> SEQ ID NO 14
<211> LENGTH: 51
<212> TYPE: DNA
<213> ORGANISM: Artificial
<220> FEATURE:
<223> OTHER INFORMATION: Synthetic; Polynucleotide for IGS9

<400> SEQUENCE: 14
aagctttaat agaggagagt gttaatatga aaaagactgc tatagcaatt g                51

<210> SEQ ID NO 15
<211> LENGTH: 52
<212> TYPE: DNA
<213> ORGANISM: Artificial
<220> FEATURE:
<223> OTHER INFORMATION: Synthetic; Polynucleotide for IGS10
```

-continued

```
<400> SEQUENCE: 15
aagctttaat agaggagagt gttaataatg aaaaagactg ctatagcaat tg            52

<210> SEQ ID NO 16
<211> LENGTH: 53
<212> TYPE: DNA
<213> ORGANISM: Artificial
<220> FEATURE:
<223> OTHER INFORMATION: Synthetic; Polynucleotide for IGS11

<400> SEQUENCE: 16
aagctttaat agaggagagt gttaataaat gaaaaagact gctatagcaa ttg           53

<210> SEQ ID NO 17
<211> LENGTH: 54
<212> TYPE: DNA
<213> ORGANISM: Artificial
<220> FEATURE:
<223> OTHER INFORMATION: Synthetic; Polynucleotide for IGS12

<400> SEQUENCE: 17
aagctttaat agaggagagt gttaataaaa tgaaaaagac tgctatagca attg          54

<210> SEQ ID NO 18
<211> LENGTH: 55
<212> TYPE: DNA
<213> ORGANISM: Artificial
<220> FEATURE:
<223> OTHER INFORMATION: Synthetic; Polynucleotide for IGS13

<400> SEQUENCE: 18
aagctttaat agaggagagt gttaataaaa atgaaaaaga ctgctatagc aattg         55

<210> SEQ ID NO 19
<211> LENGTH: 56
<212> TYPE: DNA
<213> ORGANISM: Artificial
<220> FEATURE:
<223> OTHER INFORMATION: Synthetic; Polynucleotide for IGS14

<400> SEQUENCE: 19
aagctttaat agaggagagt gttaataaaa aatgaaaaag actgctatag caattg        56

<210> SEQ ID NO 20
<211> LENGTH: 56
<212> TYPE: DNA
<213> ORGANISM: Artificial
<220> FEATURE:
<223> OTHER INFORMATION: Synthetic; Polynucleotide for IGS15

<400> SEQUENCE: 20
aagctttaat agaggagagt gttaataata aatgaaaaag actgctatag caattg        56

<210> SEQ ID NO 21
<211> LENGTH: 56
<212> TYPE: DNA
<213> ORGANISM: Artificial
<220> FEATURE:
<223> OTHER INFORMATION: Synthetic; Polynucleotide for IGS16

<400> SEQUENCE: 21
aagctttaat agaggagagt gttaaaaaaa aatgaaaaag actgctatag caattg        56

<210> SEQ ID NO 22
<211> LENGTH: 51
<212> TYPE: DNA
```

```
<213> ORGANISM: Artificial
<220> FEATURE:
<223> OTHER INFORMATION: Synthetic; Polynucleotide for IGS17

<400> SEQUENCE: 22
aagctttaat agaggagagt gttaaaatga agaaaactgc tatagcaatt g          51

<210> SEQ ID NO 23
<211> LENGTH: 52
<212> TYPE: DNA
<213> ORGANISM: Artificial
<220> FEATURE:
<223> OTHER INFORMATION: Synthetic; Polynucleotide for IGS18

<400> SEQUENCE: 23
aagctttaat agaggagagt gttaataatg aagaaaactg ctatagcaat tg         52

<210> SEQ ID NO 24
<211> LENGTH: 214
<212> TYPE: PRT
<213> ORGANISM: Artificial
<220> FEATURE:
<223> OTHER INFORMATION: Synthetic; polypeptide for light chain

<400> SEQUENCE: 24
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 25
<211> LENGTH: 229
<212> TYPE: PRT
<213> ORGANISM: Artificial
<220> FEATURE:
<223> OTHER INFORMATION: Synthetic; Polypeptide for Heavy Chain
```

```
<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 26
<211> LENGTH: 1465
<212> TYPE: DNA
<213> ORGANISM: Artificial
<220> FEATURE:
<223> OTHER INFORMATION: Sythetic; Polynucleotide for Dicistronic
      message comprising AEOS11

<400> SEQUENCE: 26
atgaaaaaga cagctatcgc aattgcagtg gccttggctg gtttcgctac cgtagcgcaa      60
gctgacattc aaatgaccca gagcccatcc agcctgagcg catctgtagg agaccgggtc     120
accatcactt gtaaagccag tcagaacgta ggtactaacg tagcctggta tcagcaaaaa     180
ccaggtaaag ccccaaaagc cctcatctac agtgcctctt tcctctatag tggtgtacca     240
tacaggttca gcggatccgg tagtggtact gatttcaccc tcacgatcag tagcctccag     300
ccagaagatt tcgccactta ttactgtcaa cagtataaca tctacccact cacattcggt     360
cagggtacta agtagaaat caaacgtacg gtagcggccc catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
```

```
ggcctgagct caccagtaac aaaaagcttt aatagaggag agtgttaaaa tgaagaaaac    720
tgctatagca attgcagtgg cgctagctgg tttcgccacc gtggcgcaag ctgaggttca    780
gctggtcgag tcaggaggcg gtctcgtgca gcctggcgga tcactgagat tgtcctgtgc    840
tgcatctggt tacgtcttca cagactatgg aatgaattgg gttagacagg ccccgggaaa    900
gggcctggaa tggatgggtt ggattaatac ttacattgga gagcctattt atgctgacag    960
cgtcaagggc agattcacgt tctctctaga cacatccaag tcaacagcat acctccaaat   1020
gaatagcctg agagcagagg acaccgcagt gtactattgt gctagaggat acagatctta   1080
tgccatggac tactggggcc agggtaccct agtcacagtc tcctcagctt ccaccaaggg   1140
cccatcggtc ttccccctgg caccctcctc caagagcacc tctgggggca gcggccct   1200 gggctgcctg gtcaaggact acttccccga accggtgacg gtgtcgtgga actcaggcgc   1260
cctgaccagc ggcgtgcaca ccttcccggc tgtcctacag tcctcaggac tctactccct   1320
cagcagcgtg gtgaccgtgc cctccagcag cttgggcacc cagacctaca tctgcaacgt   1380
gaatcacaag cccagcaaca ccaaggtcga caagaaagtt gagcccaaat cttgtgacaa   1440
aactcacaca tgcgccgcgt gatga                                         1465
```

<210> SEQ ID NO 27
<211> LENGTH: 235
<212> TYPE: PRT
<213> ORGANISM: Artificial Sequence
<220> FEATURE:
<223> OTHER INFORMATION: Synthetic

<400> SEQUENCE: 27

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asn Val Gly Thr Asn Val Ala Trp Tyr Gln Gln Lys Pro Gly Lys Ala
    50                  55                  60

Pro Lys Ala Leu Ile Tyr Ser Ala Ser Phe Leu Tyr Ser Gly Val Pro
65                  70                  75                  80

Tyr Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Tyr
            100                 105                 110

Asn Ile Tyr Pro Leu Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

```
Pro Val Thr Lys Ser Phe Asn Arg Gly Glu Cys
225                 230                 235

<210> SEQ ID NO 28
<211> LENGTH: 250
<212> TYPE: PRT
<213> ORGANISM: Artificial Sequence
<220> FEATURE:
<223> OTHER INFORMATION: Synthetic

<400> SEQUENCE: 28

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Tyr
        35                  40                  45

Val Phe Thr Asp Tyr Gly Met Asn Trp Val Arg Gln Ala Pro Gly Lys
    50                  55                  60

Gly Leu Glu Trp Met Gly Trp Ile Asn Thr Tyr Ile Gly Glu Pro Ile
65                  70                  75                  80

Tyr Ala Asp Ser Val Lys Gly Arg Phe Thr Phe Ser Leu Asp Thr Ser
                85                  90                  95

Lys Ser Thr Ala Tyr Leu Gln Met Asn Ser Leu Arg Ala Glu Asp Thr
            100                 105                 110

Ala Val Tyr Tyr Cys Ala Arg Gly Tyr Arg Ser Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Ala Ala
                245                 250
```